US012178404B2

(12) United States Patent
Montenegro et al.

(10) Patent No.: US 12,178,404 B2
(45) Date of Patent: Dec. 31, 2024

(54) MEDICAL DEVICE CONTROLLER

(71) Applicant: Boston Scientific Scimed, Inc., Maple Grove, MN (US)

(72) Inventors: Esteban Solano Montenegro, Heredia (CR); Jairo Mauricio Vargas Mena, Heredia (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 146 days.

(21) Appl. No.: 17/487,632

(22) Filed: Sep. 28, 2021

(65) Prior Publication Data

US 2022/0095892 A1    Mar. 31, 2022

Related U.S. Application Data

(60) Provisional application No. 63/084,760, filed on Sep. 29, 2020.

(51) Int. Cl.
*A61B 1/005* (2006.01)
*A61B 1/00* (2006.01)
*A61M 25/01* (2006.01)

(52) U.S. Cl.
CPC ........ *A61B 1/0052* (2013.01); *A61B 1/00105* (2013.01); *A61M 25/0136* (2013.01)

(58) Field of Classification Search
CPC ............ A61B 1/00016; A61B 1/00066; A61B 1/00128; A61B 1/0016; A61B 1/0052; A61B 1/00042; A61B 1/00105; A61B 1/00133; A61B 1/0014; A61B 2017/00398; A61M 25/0136

See application file for complete search history.

(56) References Cited

U.S. PATENT DOCUMENTS

| | | | |
|---|---|---|---|
| 8,409,080 B2 | 4/2013 | Gumbs et al. | |
| 2014/0296633 A1* | 10/2014 | Gumbs | A61B 1/0057 600/109 |
| 2016/0331213 A1* | 11/2016 | Kim | A61B 1/00048 |
| 2016/0338787 A1 | 11/2016 | Popovic et al. | |
| 2018/0098687 A1* | 4/2018 | Sholev | A61B 17/29 |
| 2019/0313881 A1* | 10/2019 | Francher | A61B 1/00103 |
| 2020/0015670 A1* | 1/2020 | Mullick | A61B 1/00119 |
| 2021/0063723 A1* | 3/2021 | Uchida | A61B 1/005 |
| 2021/0095753 A1* | 4/2021 | Uchida | G02B 23/2476 |

FOREIGN PATENT DOCUMENTS

| | | | |
|---|---|---|---|
| DE | 202010009234 U1 * | 12/2011 | ......... A61B 1/00066 |
| EP | 1 825 801 A1 | 8/2007 | |
| JP | H05300873 A * | 11/1993 | |

OTHER PUBLICATIONS

International Search Report, dated Jan. 11, 2022, in application PCT/US2021/052362 (5 pages).

* cited by examiner

*Primary Examiner* — Aaron B Fairchild
*Assistant Examiner* — Stephen Floyd London
(74) *Attorney, Agent, or Firm* — Bookoff McAndrews PLLC

(57) ABSTRACT

In one example, a controller configured for use with a medical device, may include a body configured to removably couple to the medical device. The body may include a gear configured to mate with a first actuator of the medical device; and a second actuator, and the actuation of the second actuator may be configured to initiate movement of the gear and the first actuator.

15 Claims, 3 Drawing Sheets

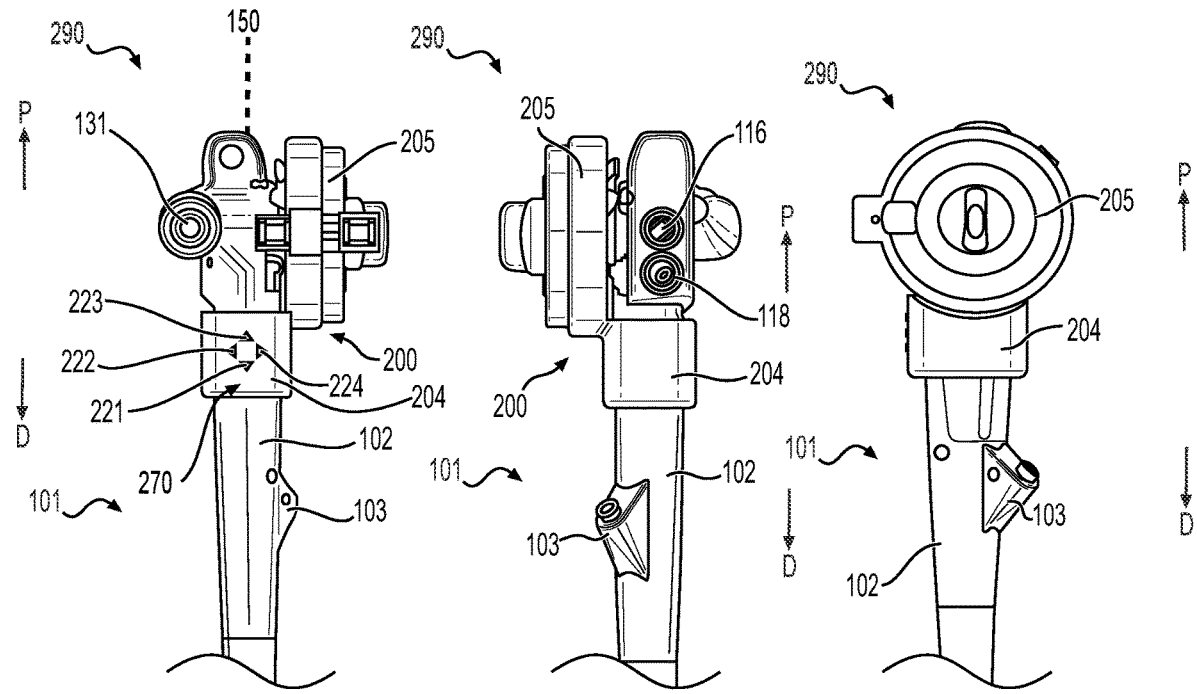
FIG. 2A  FIG. 2B  FIG. 2C
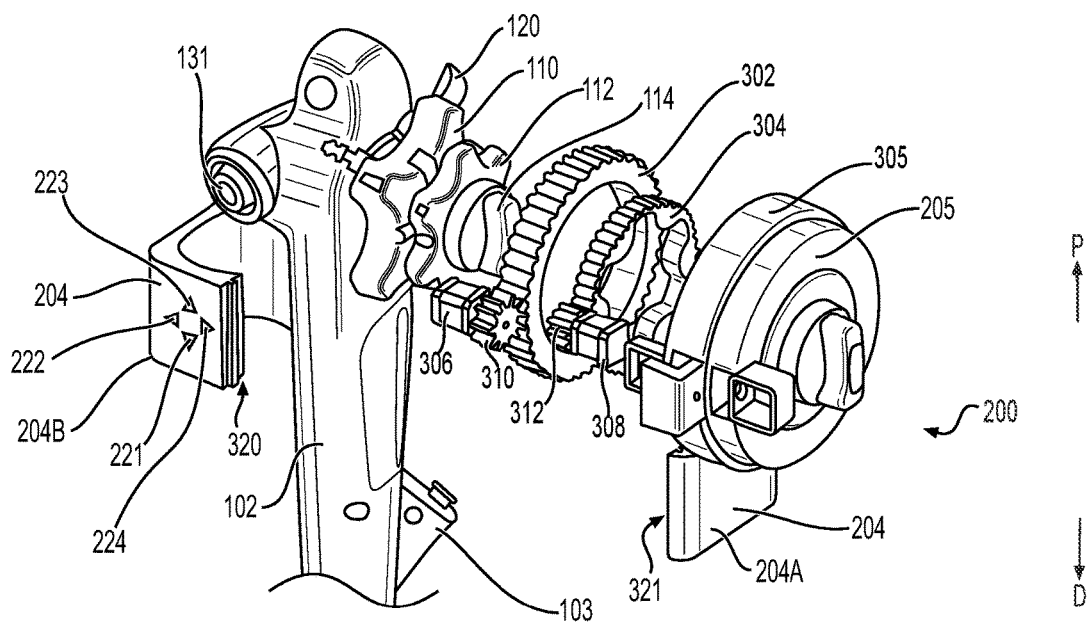
FIG. 3

MEDICAL DEVICE CONTROLLER

CROSS-REFERENCE TO RELATED APPLICATIONS

This application claims the benefit of priority from U.S. Provisional Application No. 63/084,760, filed Sep. 29, 2020, which is incorporated by reference herein in its entirety.

TECHNICAL FIELD

This disclosure generally relates to medical systems, devices, and related methods that may be used to treat a subject. Aspects of the disclosure relate to medical systems, devices, and methods for articulating a medical device during a medical procedure, among other aspects.

BACKGROUND

Physicians have adopted minimally invasive techniques, such as endoscopic procedures including endoscopic mucosal resection (EMR) and endoscopic submucosal dissection (ESD), that require the use of an endoscope or other similar medical device. An endoscope, which is a long, narrow member optionally equipped with a light, imaging equipment, and other instruments, often includes manual knobs to steer the long, narrow member through a body of a patient. During these procedures, the endoscope may be passed through a percutaneous incision, passed down the throat, or guided through the rectum to reach tissue targeted for treatment. Handling actuators or knobs of the endoscope can cause a user's hand to become tired or even cause some pain to the user after extended use of the endoscope. A user may need to develop techniques over a lengthy amount of time for skillful manipulation of an endoscope using knobs to control the steering of the scope. There is a need for a device or method to facilitate the use of endoscope knobs and/or other actuators.

The systems, devices, and methods of this disclosure may rectify some of the deficiencies described above or address other aspects of the art.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In one example, a controller configured for use with a medical device, may include a body configured to removably couple to the medical device. The body may include a gear configured to mate with a first actuator of the medical device; and a second actuator, and the actuation of the second actuator may be configured to initiate movement of the gear and the first actuator.

In other examples, the controller may include one or more of the following features. The body may further comprise a motor communicatively coupleable with the second actuator, and the motor may be configured to cause movement of the gear. The gear may be circular and includes a lumen; and the lumen may be configured to receive the first actuator. The first actuator may be a knob configured to articulate a distal portion of the medical device. The gear may be a first gear, and the body may further include a second gear configured to mate with a third actuator of the medical device; and a fourth actuator, and actuation of the fourth actuator may be configured to initiate movement of the second gear and the third actuator. The body may further include a first motor in communication with the second actuator; a third gear fixedly coupled to the first motor and configured to engage with the first gear; a second motor in communication with the fourth actuator; and a fourth gear fixedly coupled to the second motor and configured to engage with the second gear. Actuation of the second actuator may be configured to initiate clockwise rotation of the first gear and counter-clockwise rotation of the first actuator; and actuation of the fourth actuator may be configured to initiate clockwise rotation of the second gear and counter-clockwise rotation of the third actuator; and the body may further include a fifth actuator, and actuation of the fifth actuator may be configured to initiate counter-clockwise rotation of the first gear and clockwise rotation of the first actuator; and a sixth actuator, and actuation of the sixth actuator is configured to initiate counter-clockwise rotation of the second gear and clockwise rotation of the third actuator.

In other examples, the controller may include one or more of the following features. The second gear may have a larger circumference than the first gear. Each of the first gear and the second gear may include a central lumen and a plurality of gear teeth; the first actuator and the third actuator may be a first knob and a second knob, respectively; a radially-inward facing surface of the first gear may be curved to mate with the first knob; and a radially-inward facing surface of the second gear may be curved to mate with the second knob. The body may include a proximal portion and a distal portion, the distal portion may include a first portion and a second, U-shaped portion; and the first portion may be removably coupled to the second U-shaped portion. A circuit board may be electrically coupled to the second actuator. The second actuator may be positioned entirely distal to the first actuator and the gear. The first gear may be positioned within a first groove of the body; and the second gear may be positioned with a second groove of the body. The first motor and the second motor may be wirelessly connected to a circuit board positioned within the body. The second actuator may be configured to be positioned proximate to an umbilicus of the medical device when the controller is coupled to a handle of the medical device.

In other aspects, an endoscope system may include an endoscope including a handle; and a controller configured to be coupled to the handle, and uncoupled from the handle, the controller including a body, and the body comprises: a gear configured to mate with a first actuator of the handle such that rotation of the gear causes rotation of the first actuator; and a second actuator, wherein actuation of the second actuator is configured to initiate rotation of the gear and the first actuator. The body may include a distal portion configured to wrap around the handle and a proximal portion configured to cover the first actuator.

In other aspects, a method of operating an endoscope that includes a handle may include inserting at least a portion of the handle into a recess of a body of a controller to removably attach the endoscope to the controller. The recess may be configured to receive a knob of the handle, and the controller may further comprise a gear, a first actuator, and a motor. The method may further include performing an operation on a patient including initiating rotation of the knob via actuation of the first actuator.

In other aspects, the method may include one or more of the following features. The method may include at least one of (a) causing a distal portion of the endoscope to move in a right or left direction by actuating the first actuator and (b) causing a distal portion of the endoscope to move in a up or down direction by actuating the first actuator. Inserting at least a portion of the handle into the recess may include aligning a radially-inward facing surface of the gear with portions of the knob. The method may further include removing the at least a portion of the handle from the controller after performing the operation.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIGS. 2A-2C illustrate a front view, a back view, and a side view of a handle portion of an exemplary medical device system, according to aspects of this disclosure.

FIG. 3 illustrates an exploded perspective view of components of the medical device system in FIGS. 2A-2C, according to aspects of this disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Embodiments of this disclosure include devices, systems, and methods to facilitate operation of an endoscope or other medical device. In some examples the devices, systems and/or methods discussed herein may be utilized during endoscopic procedures, such as mucosal resection (EMR) and/or endoscopic submucosal dissection (ESD) procedures. Devices, systems, and methods of this disclosure may be utilized with an endoscope, bronchoscope, colonoscope, gastroscope, duodenoscope, or any medical device known in the art. In some examples, devices, systems, and methods of this disclosure may be utilized in an endoscopic procedure including insertion of the endoscope through a bodily orifice, for example, the nose, mouth, or anus, and steering the endoscope through a body of a patient, including the esophagus, stomach, duodenum, large intestine, small intestine, and any other area of the patient's body for treatment. Embodiments of this disclosure however are not limited to any specific procedure or use in any particular portion of the body.

Reference will now be made in detail to examples of this disclosure described above and illustrated in the accompanying drawings. Wherever possible, the same reference numbers will be used throughout the drawings to refer to the same or like parts.

Figure 1:
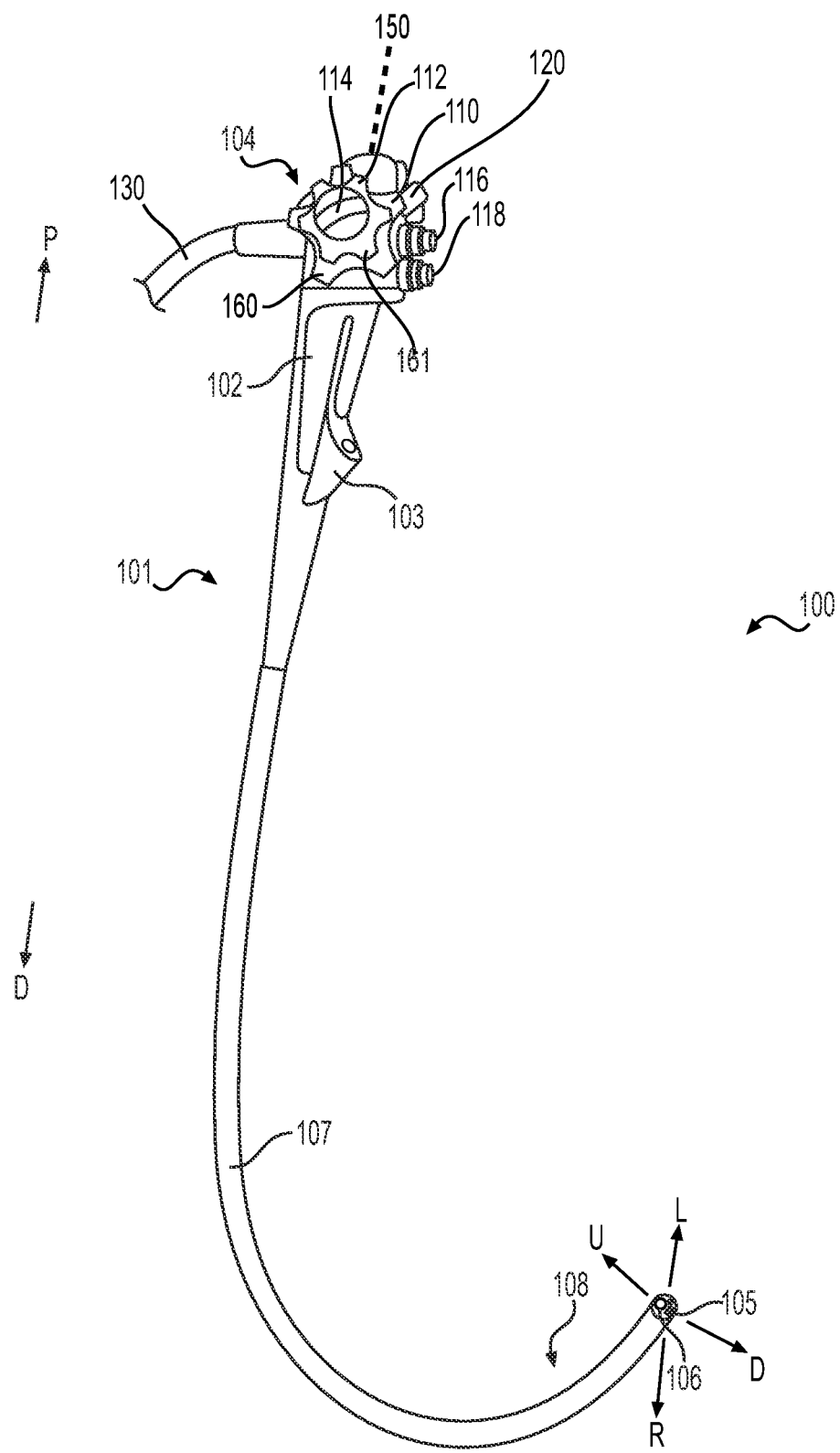
FIG. 1 illustrates a perspective view of a medical device, according to aspects of this disclosure.

FIG. 1 illustrates a perspective view of an exemplary endoscope 101. Although the medical device shown in FIG. 1 is an endoscope 101, any other similar insertion device may be used, such as a bronchoscope, colonoscope, gastroscope, duodenoscope, etc. Endoscope 101 may include a handle 102, actuators 104, and a body 107 extending from handle 102 to a distal end 108. A working channel 106 may extend from a working channel port 103 positioned on the handle 102 to an opening at distal end 108. Distal end 108 of endoscope 101 may also include a camera 105, and movement of distal end 108 and functionality of camera 105 may be controlled via one or more actuators 104 on handle 102. Actuators 104 may include a first articulation knob 110, a second articulation knob 112, a first locking actuator 120, a second locking actuator 114, a fluid jet actuator 116, and an air vacuum actuator 118. While fluid jet actuator 116 and an air vacuum actuator 118 are identified as such, each of these actuators may actuate any function of endoscope 101 and is not limited to fluid jet actuation or air vacuum actuation. An umbilicus 130 may connect handle 102 with a control unit (not shown), and the control unit may be used to control camera 105, process images, control light, or any other feature of endoscope 101. Umbilicus 130 may also connect handle 102 with a fluid source and/or a vacuum source.

In some examples, actuation of first articulation knob 110 may move distal portion 108 of body 107 in a right or left direction, shown as R and L arrows in FIG. 1, and articulation of second articulation knob 112 may move distal portion 108 in an up or down direction, shown as U and D arrows in FIG. 1. In other examples, actuation of first articulation knob 110 may move distal portion 108 in an up or down direction, and actuation of second articulation knob 112 may move distal portion 108 in a right or left direction. In some examples, distal portion 108 may bend when either first articulation knob 110 and/or second articulation knob 112 is actuated. First locking actuator 120 may be configured to lock first articulation knob 110 in a position and not allow rotation of first articulation knob 110 when first locking actuator 120 is actuated. Second locking actuator 114 may be configured to lock second articulation knob 112 in a position and not allow rotation of second articulation knob 112 when second locking actuator 114 is actuated. In other examples, instead of two locking actuators 120, 114, only one locking actuator may be used to lock both first articulation knob 110 and second articulation knob 112. Second articulation knob 112 may be radially-outer from first articulation knob 110 relative to a central longitudinal axis 150 of endoscope 101, and second locking actuator 114 may be radially outer from second articulation knob 112 relative to central longitudinal axis 150. Actuators 104 may be positioned at a proximal portion of handle 102 and may be proximate to umbilicus 130, fluid jet actuator 116, and air vacuum actuator 118.

In some examples, each of first articulation knob 110 and second articulation knob 112 may be generally circular and may include several prongs extending radially outward from a center of the articulation knob, and curved surfaces may extend between each prong forming a star-shaped configuration. In some examples, the first articulation knob 110 may include five prongs 160 and the second articulation knob 112 may include six prongs 161. The prongs 160, 161 of each articulation knob 110, 112 may facilitate rotation of the knobs by the user.

FIGS. 2A, 2B, and 2C illustrate front, back and side views of a medical system 290 including controller 200 coupled to endoscope 101. These FIGS. 2A-2C) show only the handle 102, other more distal portions are omitted. In some examples controller 200 can be separate and distinct from endoscope 101 (to be re-used with that endoscope 101 or other devices), or can be integral with and fixed to endoscope 101, for use only with that endoscope 101. Controller 200 may include a distal portion 204 and a proximal portion 205. Distal portion 204 may be substantially cylindrical and configured to couple to a portion of endoscope handle 102 distal to actuators 104 and umbilicus input 131, and proximal of working channel port 103. In some examples, distal portion 204 may be configured to extend completely around handle 102 about central longitudinal axis 150. In other examples, distal portion 204 may extend only partially around handle 102 about central longitudinal axis 150. Distal portion 204 may include actuators 221-224 positioned on a radially-outward facing surface 270 of distal portion 204 and configured to be actuated by one or more of a user's fingers. Actuators 221-224 may be triangular and may be pointed in a proximal direction (actuator 223), a distal direction (actuator 221), a left or first lateral direction (actuator 222), and a right or second lateral direction opposite the first lateral direction (actuator 224). Although actuators 221-224 are shown triangular in FIG. 2A, they are not so limited and may be shaped in any suitable shape or configuration. Actuators 221-224 may be buttons that are pressed by a user. In other examples, actuators 221-224 may be replaced with a joystick actuator that is pivotable relative to distal portion 204. In some examples, controller 200 may not include actuators 221-224 and may communicate, wirelessly or via a cable, with a control unit connected to endoscope 101, and instructions may be sent from the control unit to a circuit board, processor, and/or motors 306, 308 of controller 200. Alternatively, controller 200 may communicate, wirelessly or via a cable, with a handheld remote controller, and instructions from the remote controller may be sent to a circuit board, processor, and/or motors 306, 308 of controller 200. Distal portion 204 may be sized to allow a user to wrap one or more fingers around both handle 102 and distal portion 204 when distal portion 204 is coupled to handle 102.

Proximal portion 205 may be fixedly coupled to distal portion 204. In some examples, proximal portion 205 and a portion 204A (shown in FIG. 3) of distal portion 204 may form a unitary body. Proximal portion 205 may extend radially outward from distal portion 204 relative to axis 150. Proximal portion 205 may be configured to receive one or more actuators 104. In some examples, proximal portion 205 may be configured to cover first articulation knob 110, second articulation knob 112, first locking actuator 120, and second locking actuator 114 when coupled to handle 102. Proximal portion 205 may taper as it extends outward from axis 150. As shown in FIG. 2B, proximal portion 205 may be spaced from fluid jet actuator 116 and an air vacuum actuator 118 to allow a user access to actuators 116, 118 during operation of controller 200 and endoscope 101. Proximal portion 205 may be offset from a central longitudinal axis of distal portion 204.

FIG. 3 illustrates an exploded perspective view of handle 102 and components of controller 200. As shown in FIG. 3, distal portion 204 may include a first portion 204A fixedly coupled to proximal portion 205, and a second portion 204B. Second portion 204B may removably couple to first portion 204A (as shown in FIGS. 2A-2C). Second portion 204B may be U-shaped and may include a protrusion 320 that may be configured to snap-fit into a groove 321 of first portion 204A to removably couple first portion 204A to second portion 204B. In some examples, protrusion 320 may be configured to electrically couple to groove 321 to electrically connect first portion 204A with second portion 204*b*, which may provide connection between actuators 221-224 and other components of controller 200, such as motors 306, 308. In some examples, second portion 204B may include a circuit board, a control panel, and/or a power cord positioned within second portion 204B. In some examples, controller 200 may include an electrical cord to connect electrical components of controller 200, e.g. motors 306, 308, circuit board, etc., to a power outlet. A circuit board/processor may be positioned within any portion of device 200 and may be configured to connect to motors 306, 308 and actuators 221-224. In some examples, motors 306, 308 may be in communication with one or more circuit boards/processors within controller 200 and/or outside of medical device, such as within a control unit connected to endoscope 101 or a handheld remote controller. In some examples, controller 200 may rely on a control unit (separate from controller 200 and connected to controller 200) to control motors 306, 308. In some examples, a wire (not shown) may connect portion 204B with portion 204A or proximal portion 205 of medical device.

Figure 4:
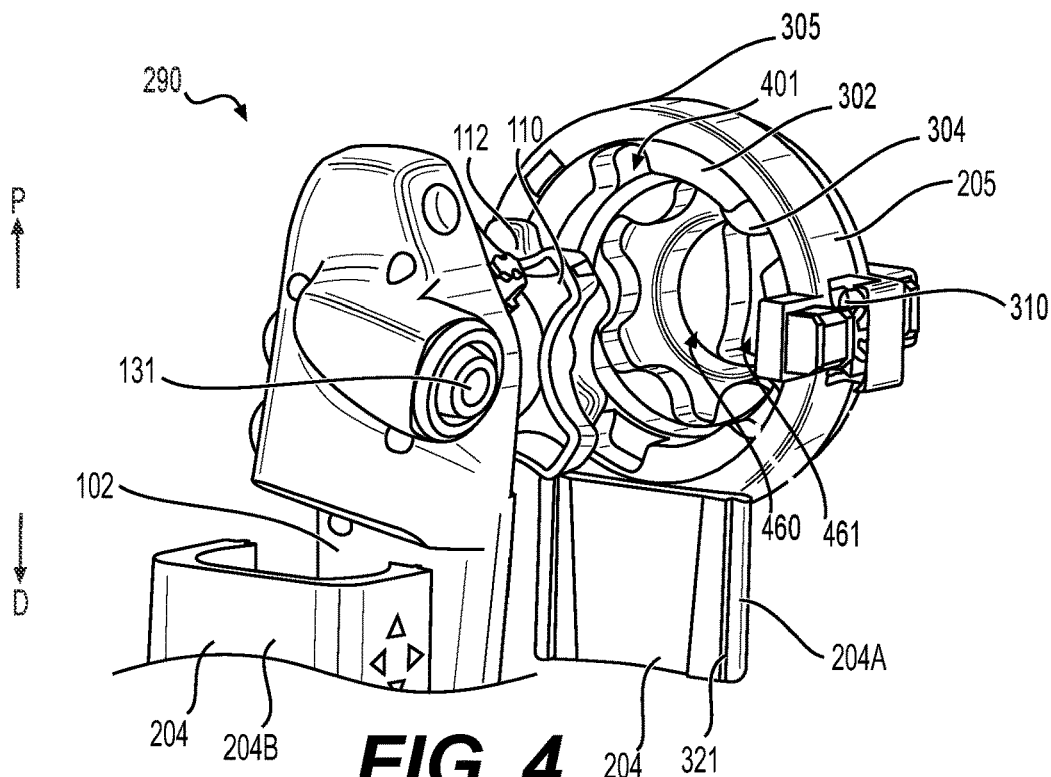
FIG. 4 illustrates an exploded perspective view of the medical device system of FIGS. 2A-2C, according to aspects of the disclosure.

Proximal portion 205 may include an exterior body 305 configured to receive a first gear member 302, a second gear member 304, a third gear member 310, a fourth gear member 312, a first motor 306, and a second motor 308. Second gear member 304 may be positioned adjacent to first gear member 302 and may be radially outer from first gear member 302 relative to axis 150. Each motor 306, 308 may be configured to be positioned within a portion of body 305. FIG. 4 shows first gear member 302, second gear member 304, third gear member 310, fourth gear member 312, first motor 306, and second motor 308 positioned within body 305.

As shown in FIG. 4, body 305 may include a recess 460, and each of first gear member 302 and second gear member 304 may be positioned within recess 460. In some examples, each of first gear member 302 and second gear member 304 may be rotatably coupled to body 305 (gear members 302, 304 rotate within and relative to body 305) and may be positioned within recess 460 of body 305 such that portions of first gear member 302 and second gear member 304 extend outward from an exterior surface of body 305. Recess 460 may be tapered and may be configured to receive actuators 104 of endoscope handle 102. Portions of body 305 forming recess 460 may include two grooves (not shown), one of the grooves may receive first gear member 302, and the other groove may receive second gear member 304. Each of these grooves may be configured to allow each gear member 302, 304 to move within the groove and prevent movement of the gear member 302, 304 to a position outside of the respective groove the gear member 302, 304 is positioned within. A second recess 461 of body 305 may be configured to receive second locking actuator 114 and may prevent rotation of second locking actuator 114 when controller 200 is coupled to endoscope 101. The contours of surfaces defining recess 461 may closely match and mate with the outer contours of actuator 114, thereby inhibiting movement of actuator 114 within recess 461. Motors 306, 308 may be fixedly coupled to body 305, and gear members 310, 312 may be positioned to allow interaction with gear members 302, 304 while being fixedly coupled to one of motors 306, 308. The structure and position of gear members 302, 304 will be discussed in further detail below.

Figures 5, 6:
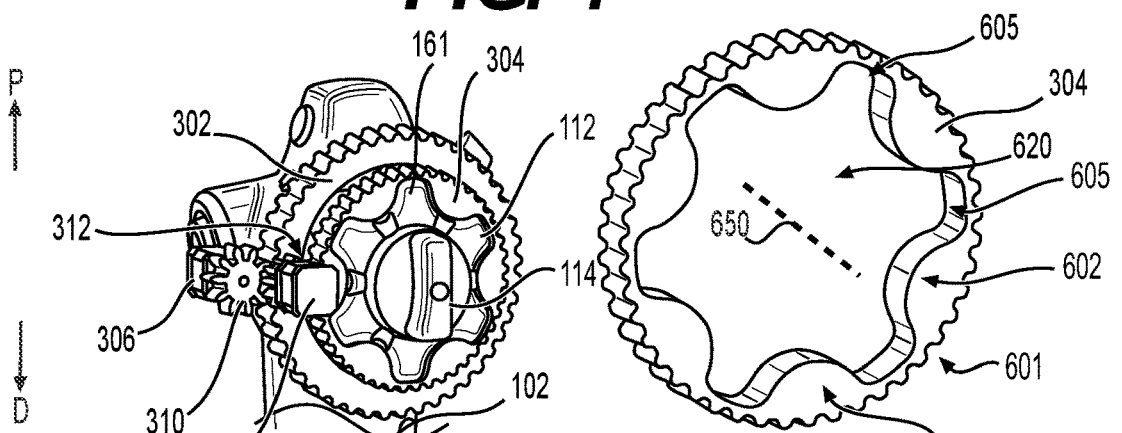
FIGS. 5-8 illustrate perspective views of components of the medical device system of FIGS. 2A-2C, according to aspects of the disclosure.

FIG. 5 illustrates a perspective view of a proximal portion of handle 102 with components of controller 200 coupled to first articulation knob 110 and second articulation knob 112 of handle 102, and body 305 removed (not shown). As shown in FIG. 6, second gear member 304 may include a central lumen 620, and central lumen 620 may be shaped to receive second articulation knob 112. Second gear member 304 may include gear teeth 601 extending around a radially-outer surface of second gear member 304 relative to a central axis 650. Central axis 650 may extend through the center of central lumen 620, and second gear member 304 may extend circumferentially around central axis 650. Second gear member 304 may include curved protrusions 602 extending radially inwards towards axis 650, and recessed portions 605 may connect each curved protrusion 602 to each other extending around axis 650. Curved protrusions 602 and recessed portions 605 may be configured to mate with second articulating knob 112, and specifically prongs 161 of second articulating knob 112 may be aligned with recesses 605 (shown in FIG. 5). By providing protrusions 602 and recesses 605 in second gear member 304, second gear member 304 may mate with second articulating knob 112 such that rotation of second gear member 304 may cause rotation of second articulating knob 112.

As shown in FIGS. 3 and 5, gear teeth 601 of second gear member 304 may be configured to engage with gear teeth of fourth gear member 312. For example, motor 308 may drive fourth gear member 312 to rotate fourth gear member 312, which may cause gear teeth of fourth gear member 312 to engage gear teeth 601 of second gear member 304 and rotate second gear member 304. In some examples, motor 308 may be electronically connected, via physical connection or wireless connection, to one or more of actuators 221-224, and actuations of the one or more actuators 221-224 may cause motor 308 to rotate fourth gear member 312, and thus cause rotation of second gear member 304. For example, actuation (e.g. pressing) of actuator 221 may initiate clockwise rotation of fourth gear member 312 via motor 308, and thus cause counter-clockwise rotation of second gear member 304; and actuation (e.g. pressing) of actuator 223 may initiate counter-clockwise rotation of fourth gear member 312 via motor 308, and thus cause clockwise rotation of second gear member 304. While second gear member 304 is shown with curved protrusions 602 and recesses 605, other embodiments of first gear member 302 may include a different shape configured to mate with second articulation knob 112. The circumference and diameter of first gear member 302 may be larger than the circumference and diameter, respectively, of second gear member 304. In some examples, motor 308 may be connected to one or more actuators 221-224 via a circuit board of controller 200 and/or via a control unit.

Figures 7, 8:
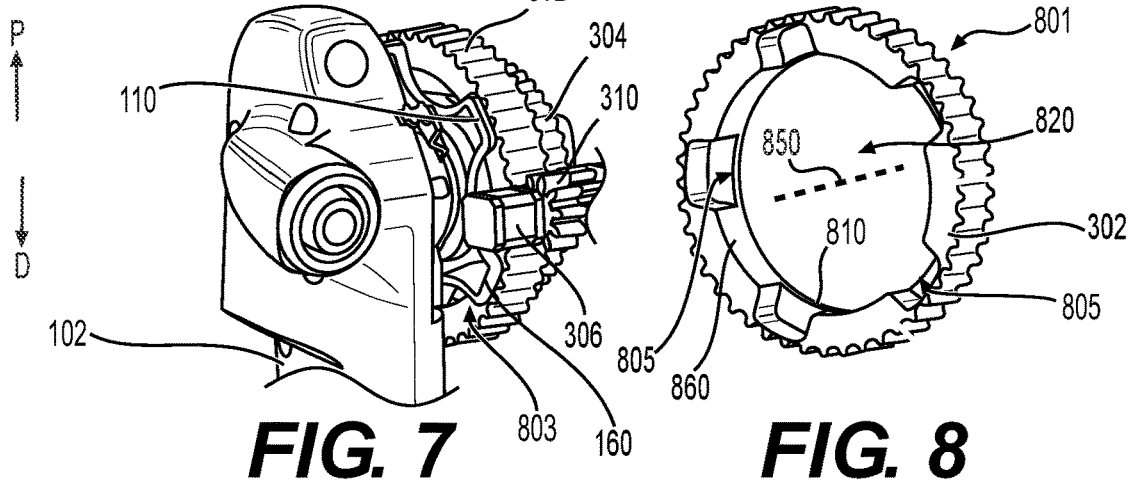

FIG. 7 illustrates a perspective view of a proximal portion of handle 102 with components of controller 200 coupled to first articulation knob 110 and second articulation knob 112 of handle 102. As shown in FIG. 8, first gear member 302 may include a central lumen 820, and central lumen 820 may be shaped to receive first articulation knob 110. First gear member 302 may include gear teeth 801 extending around a radially-outer surface of first gear member 302 relative to a central axis 850. Central axis 850 may extend through the center of central lumen 820, and first gear member 302 may extend circumferentially around central axis 850. Central axis 850 may be aligned with central axis 650. First gear member 302 may include a circular, radially-inward facing surface 860 relative to axis 850. Recessed portions 805 may be circumferentially spaced around a radially-inward facing surface 860. Recessed portions 805 may be configured to mate with first articulating knob 110, and specifically prongs 160 of first articulating knob 110 may be aligned with recesses 805 (shown in FIG. 7). By providing recesses 805 in first gear member 302, first gear member 302 may mate with first articulating knob 110 such that rotation of first gear member 302 may cause rotation of first articulating knob 110.

As shown in FIGS. 3 and 7, gear teeth 801 of first gear member 302 may be configured to engage with gear teeth of third gear member 310. For example, motor 306 may drive third gear member 310 to rotate third gear member 310, which may cause gear teeth of third gear member 310 to engage gear teeth 801 of first gear member 302 and rotate first gear member 302. In some examples, motor 306 may be electronically connected, via physical connection or wireless connection, to one or more of actuators 221-224, and actuations of the one or more actuators 221-224 may cause motor 306 to rotate third gear member 310, and thus cause rotation of first gear member 302. For example, actuation (e.g. pressing) of actuator 222 may initiate clockwise rotation of third gear member 310, and thus cause counter-clockwise rotation of first gear member 302; and actuation (e.g. pressing) of actuator 224 may initiate counter-clockwise rotation of third gear member 310, and thus cause clockwise rotation of first gear member 302. While first gear member 302 is shown with recesses 805 other embodiments of first gear member 302 may include a different shape configured to mate with first articulation knob 110. In some examples, motor 306 may be connected to one or more actuators 221-224 via a circuit board of controller 200 and/or via a control unit.

In operation, controller 200 may be utilized with endoscope 101 or a similar medical device. A user may first couple controller 200 to handle 102 of endoscope 101. To couple controller 200 to endoscope 101, a user may position portion 204B of controller 200 around handle 102. The user may then insert actuators 104 of endoscope 101 into recess 460 of controller 200, and mate each of first articulation knob 110 and second articulation knob 112 with the first gear member 302 and second gear member 304, respectively. The user may snap or otherwise couple portion 204B to portion 204A of medical device, which may fixedly couple controller 200 to endoscope handle 102. Once controller 200 is coupled to handle 102 of endoscope 101, the user may proceed with an endoscopic procedure by inserting body 107 of endoscope 101 into a patient's body. To maneuver the body 107 of endoscope 101 through the patient's body, a user may actuate actuators 221-224 to cause distal portion 108 to bend, pivot, or otherwise move in a right, left, up, or down direction (R, L, U, or D shown in FIG. 1). For example, the user may push on actuator 222 to send electronic instructions to motor 306, and motor 306 may then rotate third gear member 310 to rotate first gear member 302, which may then cause first articulation knob 110 to rotate and cause upward (U) movement of distal portion 108 of endoscope 101. Pushing on actuators 221, 223, 224 similarly cause right, left, and down movements of distal portion 108, in the manners described above. When the user is not actuating any of actuators 221-224, controller 200 may hold first and second articulation knobs 110, 112 in place, which may allow the user to rest his hand without releasing an articulation knob 110, 112 and potentially causing unwanted movement of distal portion 108 during the operation. Once the operation is completed and the user has removed endoscope 101 from the patient, the user may remove controller 200 from endoscope handle 102 by uncoupling portions 204A and 204B from each other. Controller 200 may then be used in subsequent procedures with the same or other medical devices.

It also should also be understood that one or more aspects of any of the medical devices, systems, and methods described herein may be used for maneuvering a medical device through any part of the human body. For example, any of the medical devices described herein may be used in medical procedures, including, for example, urologic, pulmonary, and endoscopic procedures, and/or other procedures requiring insertion of a medical device into a patient's body.

Various aspects discussed herein may help reduce procedure time, decrease medical device user fatigue, increase accuracy of maneuvering medical devices, and facilitate operation of endoscopes and other related medical devices. The devices and methods of this disclosure may facilitate the use of endoscope knobs and/or other actuators to mitigate user fatigue and/or user pain caused from manipulating the endoscope knobs and/or other actuators.

Although the exemplary embodiments described above have been disclosed in connection with endoscopes, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of this disclosure as defined by the following claims.

We claim:

1. A controller configured for use with a medical device, comprising:
   a body configured to removably couple to the medical device, wherein the body comprises:
   a first body including:
   a first gear configured to mate with a first actuator of the medical device;
   a second gear configured to mate with a third actuator of the medical device; and
   a second body including:
   a second actuator, wherein actuation of the second actuator is configured to initiate movement of the first gear and the first actuator; and
   a fourth actuator, wherein actuation of the fourth actuator is configured to wirelessly initiate movement of the second gear and the third actuator;
   wherein the second body is U-shaped and configured to (i) directly couple to and abut a handle of the medical device and (ii) wirelessly connect to the first body to initiate movement of the first gear and the first actuator.

2. The controller of claim 1, wherein the body further comprises a motor communicatively coupleable with the second actuator, and the motor is configured to cause movement of the first gear.

3. The controller of claim 1, wherein the first gear is circular and includes a lumen; wherein the lumen is configured to receive the first actuator.

4. The controller of claim 1, wherein the first actuator is a knob configured to articulate a distal portion of the medical device.

5. The controller of claim 1, wherein the body further comprises:
   a first motor in communication with the second actuator;
   a third gear fixedly coupled to the first motor and configured to engage with the first gear;
   a second motor in communication with the fourth actuator; and
   a fourth gear fixedly coupled to the second motor and configured to engage with the second gear.

6. The controller of claim 5, wherein actuation of the second actuator is configured to initiate clockwise rotation of the first gear and counter-clockwise rotation of the first actuator; wherein actuation of the fourth actuator is configured to initiate clockwise rotation of the second gear and counter-clockwise rotation of the third actuator; and wherein the body further comprises:
   a fifth actuator positioned on the second body, wherein actuation of the fifth actuator is configured to wirelessly initiate counter-clockwise rotation of the first gear and clockwise rotation of the first actuator; and
   a sixth actuator positioned on the second body, wherein actuation of the sixth actuator is configured to wirelessly initiate counter-clockwise rotation of the second gear and clockwise rotation of the third actuator.

7. The controller of claim 5, wherein the first motor and the second motor are wirelessly connected to a circuit board positioned within the second body.

8. The controller of claim 1, wherein the second gear has a larger circumference than the first gear.

9. The controller of claim 1, wherein each of the first gear and the second gear includes a central lumen and a plurality of gear teeth; wherein the first actuator and the third actuator are a first knob and a second knob, respectively;
wherein a radially-inward facing surface of the first gear is curved to mate with the first knob; and wherein a radially-inward facing surface of the second gear is curved to mate with the second knob.

10. The controller of claim 1, wherein the second body is configured to couple to a distal portion of the first body.

11. The controller of claim 1, further comprising a circuit board electrically coupled to the second actuator.

12. The controller of claim 1, wherein the second actuator is positioned entirely distal to the first actuator and the first gear.

13. The controller of claim 1, wherein the first gear is positioned within a first groove of the first body; and wherein the second gear is positioned with a second groove of the first body.

14. The controller of claim 1, wherein the second actuator is configured to be positioned proximate to an umbilicus of the medical device when the controller is coupled to the handle of the medical device.

15. An endoscope system comprising:
an endoscope including a handle; and
a controller configured to be coupled to the handle, and uncoupled from the handle, the controller comprising:
a body, wherein the body comprises:
a gear configured to mate with a first actuator of the handle such that rotation of the gear causes rotation of the first actuator;
a second actuator, wherein actuation of the second actuator is configured to initiate rotation of the gear and the first actuator;
a first recess configured to receive a first locking actuator of the endoscope and prevent rotation of the first locking actuator when the body is coupled to the endoscope; and
a second recess configured to receive a second locking actuator of the endoscope and prevent rotation of the second locking actuator when the body is coupled to the endoscope;
wherein the body includes a distal portion configured to wrap around the handle and a proximal portion configured to cover the first actuator.

\* \* \* \* \*